United States Patent [19]

Tadanier et al.

[11] 4,232,147
[45] Nov. 4, 1980

[54] 4-N-ACYLFORTIMICIN B-1,5-CARBAMATES

[75] Inventors: John S. Tadanier; Jerry R. Martin, both of Waukegan, Ill.

[73] Assignee: Abbott Laboratories, North Chicago, Ill.

[21] Appl. No.: 79,143

[22] Filed: Sep. 26, 1979

[51] Int. Cl.³ .......................................... C07H 17/00
[52] U.S. Cl. .................................... 536/4; 536/17 R; 544/92; 424/180
[58] Field of Search ...................... 536/4, 17; 544/92; 424/180, 181

[56] References Cited

U.S. PATENT DOCUMENTS

| | | | |
|---|---|---|---|
| 4,091,032 | 5/1979 | Tadanier et al. | 260/345.8 R |
| 4,124,756 | 11/1978 | Martin et al. | 536/17 R |
| 4,169,198 | 9/1979 | Martin et al. | 536/17 R |
| 4,176,617 | 11/1979 | Martin et al. | 424/180 |
| 4,183,920 | 1/1980 | Kurath et al. | 424/180 |
| 4,187,296 | 2/1980 | Tadanier et al. | 424/180 |
| 4,187,297 | 2/1980 | Martin et al. | 424/180 |
| 4,187,298 | 2/1980 | McAlpine | 536/17 R |
| 4,187,299 | 2/1980 | Post | 536/17 R |

*Primary Examiner*—John D. Randolph
*Attorney, Agent, or Firm*—Gildo E. Fato; Robert L. Niblack; Joyce R. Niblack

[57] ABSTRACT

4-N-acylfortimicin B-1,5-carbamates represented by the formula

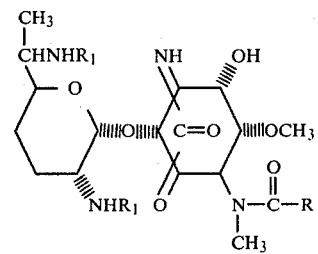

wherein R is acyl and $R_1$ is hydrogen or benzyloxycarbonyl.

7 Claims, No Drawings

4-N-ACYLFORTIMICIN B-1,5-CARBAMATES

BACKGROUND OF THE INVENTION

Aminoglycoside antibiotics are a useful class of antibiotics which include streptomicins, neomycins, kanamycins, gentamicins, tobramycins, amikacin and the more recently discovered fortimicins. It is known that chemical modification of the aminoglycoside antibiotics can result in altered antibacterial and pharmacological properties of the aminoglycosides. For example, certain modifications in the getamicin and kanamycin family of antibiotics provide compounds which are less toxic than the parent antibiotics. Further, certain modifications in the gentamicin and kanamycin series have been found to alter the antibiotic spectra advantageously either by increasing the intrinsic activity or increasing the activity against resistant strains.

While the fortimicins are a relatively new family of antibiotics, chemical modifications have been found to advantageously modify the properties of these antibiotics as well. One such modification has provided a series of 2-deoxyfortimicins, 2-deoxyfortimicin B, an intermediate for producing the antibiotic 2-deoxyfortimicin A and 2-deoxyfortimicin B derivatives. These compounds are disclosed and claimed in commonly assigned, copending, allowed U.S. patent application Nos. 863,006 and 863,009 (now U.S. Pat. No. 4,169,198, issued Mar. 11, 1980) both filed on Dec. 21, 1979.

The present invention provides intermediates which are useful in the preparation of 2-deoxyfortimicin B.

SUMMARY OF THE INVENTION

The present invention provides a series of fortimicin intermediates, 4-N-acyl fortimicin B-1,5-carbamates. The compounds are useful as intermediates in the preparation of 2-deoxyfortimicin B.

DETAILED DESCRIPTION OF PREFERRED EMBODIMENTS

The compounds of this invention, 4-N-acylfortimicin B-1,5-carbamates, are represented by the formula

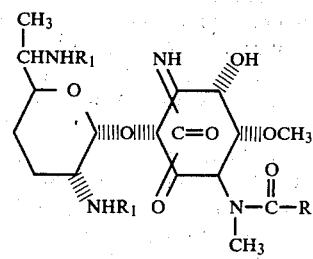

wherein R is acyl and $R_1$ is hydrogen or benzyloxycarbonyl.

The term "acyl", as used herein, refers to groups represented by the formula

wherein R is loweralkyl, i.e. acetyl, propionyl, butyryl, valeryl, etc.

The term "loweralkyl" refers to straight or branched chaim alkyl radicals having from 1 to 6 carbon atoms, i.e. methyl, ethyl, n-propyl, iso-propyl, n-butyl, sec-butyl, tert-butyl, n-hexyl, n-pentyl, etc.

The preparation of the compounds of this invention is summarized in the following reaction schemes and disclosed in detail in the following examples.

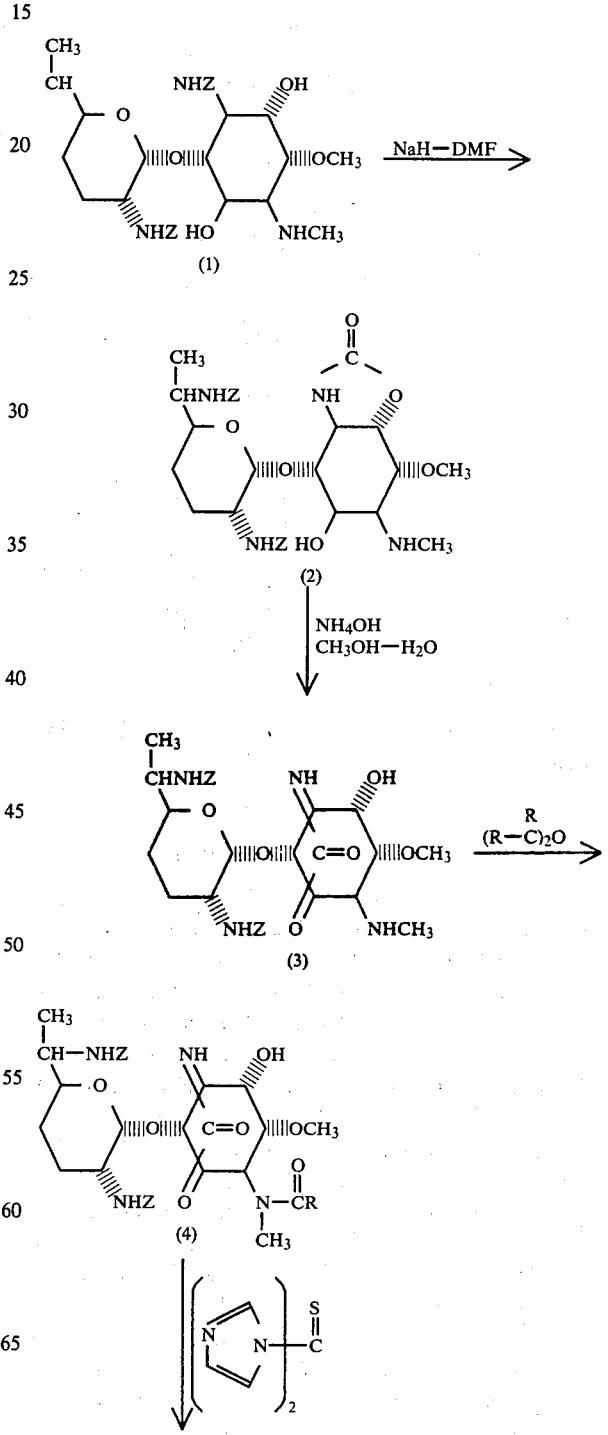

-continued

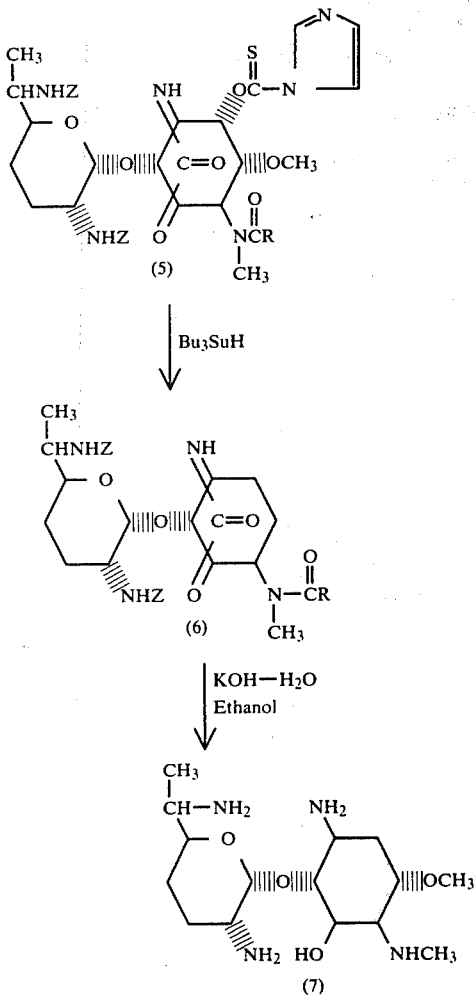

The following Examples further illustrate the present invention.

EXAMPLE 1

1,2',6'-Tri-N-benzyloxycarbonylfortimicin B(1)

To a stirred solution of 2.0 g of fortimicin B, 30 ml of water and 60 ml of methanol, cooled in an ice bath, is added 4.44 g of N-(benzyloxycarbonyloxy)succinimide. Stirring is continued at 0° C. for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromatographed on silica gel. Elution with a solvent system composed of chloroform-methanol-ammonium hydroxide [234:1.4:0.1(v/v/v)] gives 1.05 g of product (1): $[\alpha]_D^{25} -16.5°$ (c 1.0, $CH_3OH$); IR($CDCl_3$)1712 and 1507 $cm^{-1}$; NMR ($CDCl_3$) $\delta 1.03$ ($C_{6'}$—$CH_3$, $J_{6',7'}=6.0$ HZ), 2.32 ($C_4$—$NCH_3$), 3.41 ($OCH_3$).

Analysis Calcd. for $C_{39}H_{50}N_4O_{11}$: C, 62.39; H, 6.71; N, 7.46 Found: C, 62.16; H, 6.76; N, 7.43

EXAMPLE 2

2,',6'-Di-N-benzyloxycarbonylfortimicin B-1,2-carbamate(2)

A. 1,2',6'-Tri-N-benzyloxycarbonylfortimicin B-4,5-formaldehyde oxazolidine

A solution of 16.0 g of 1,2',6'-tri-N-benzyloxycarbonylfortimicin B(1), 8 ml of 37% aqueous formaldehyde, and 400 ml of methanol is allowed to stand overnight at room temperature. The major portion of the solvent is evaporated under reduced pressure. Residual water is removed by co-distillation with benzene leaving 16.3 g of the desired product as a white glass: NMR ($CDCl_3$ $\delta 1.17d$ (J=6.5 Hz) ($C_{6'}$—$CH_3$), 2.28 ($NCH_3$), 2.80q ($J_{3,4}=6.5$ Hz, $J_{4,5}=2.0$ Hz) ($C_4$—H); 3.5 ($OCH_3$); 3.81d, 4.60d ($OCH_2$—N) (J=2.3 Hz).

B. 2',6'-Di-N-benzyloxycarbonylfortimicin B-1,2-carbamate 4,5-formaldehyde oxazolidine A solution of 16.3 g of the above-prepared material, 16.3 g of 1,5-diazobicyclo[5.4.0]undecene-5, and 815 ml of benzene is heated under reflux for four days. The resulting solution is cooled to room temperature, 250 ml of water are added and the mixture stirred at room temperature for one hour. The mixture is then shaken with 700 ml of 5 percent aqueous sodium bicarbonate. The aqueous phase is separated and extracted with 500 ml of benzene. The benzene solutions are washed with three 500 ml portions of saturated aqueous sodium chloride, combined and dried over magnesium sulfage. Evaporation of the benzene under reduced pressure yields 15.3 g of the desired product; IR($CDCl_3$) 3459, 1762, 1709 $cm^{-1}$.

C. 2',6'-Di-N-benzyloxycarbonylfortimicin B-1,2-carbamate(3)

A solution of 15.3 g of the above-prepared intermediate, 5.2 g of hydroxylamine hydrochloride, 14.5 ml of acetic acid and 900 ml of methanol are heated under reflux for 1 hour. The solution is cooled to room temperature and the major portion of the methanol evaporated under reduced pressure. The residue is shaken with a mixture of one liter of chloroform and one liter of 1:1 (v/v) concentrated ammonium hydroxide-water. The aqueous layer is separated and the chloroform solution is washed with 500 ml of water. The aqueous solutions are extracted with 500 ml of chloroform. The chloroform solutions are combined and dried over magnesium sulfate. Evaporation of the chloroform under reduced pressure leaves 14.8 g of crude 2,6'-di-N-benzyloxycarbonylfortimicin B-1,2-carbamate (3). The latter is chromatographed on a column of 850 g of silica gel, packed and eluted with a solvent system prepared from chloroformmethanol [19.5–0.5(v/v)] to yield 7.9 g of pure product: $[\alpha]_D^{21} +27°$ (c 1%, $CH_3OH$); NMR ($CDCl_3$) $\delta 1.14$ d (J=6.5 Hz) ($C_{6'}$—$CH_3$), 2.39 ($NCH_3$), 3.45 ($OCH_3$); IR ($CDCl_3$) 3439, 3411, 3353, 1765, 1705 $cm^{-1}$.

EXAMPLE 3

2',6'-Di-N-benzyloxycarbonylfortimicin B-1,5-carbamate(3)

A solution of 7.22 g of crude 2',6'-di-N-benzyloxycarbonylfortimicin B-1,2-carbamate(2), prepared as described in Example 2, 360 ml of methanol and 180 ml of 1:4 (v/v) concentrated ammonium hydroxide-water, is kept at room temperature for two days. The major portion of the methanol is evaporated under reduced pressure, and the residue is shaken with a mixture of 300 ml of chloroform and 400 ml of 5 percent aqueous sodium bicarbonate. The chloroform solution is separated and washed with 400 ml of water. The aqueous solutions are washed in series with three 200 ml portions of chloroform. The chloroform solutions are combined and the chloroform evaporated under reduced pressure leaving 7.0 g of light orange glass. Chromatography of the latter on a column of 450 g of silica gel packed and eluted with a solvent system composed of methylene chloride-methanol-concentrated ammonium hydroxide [20:2:0.1(v/v/v)] gave pure 2',6'-di-N-benzyloxycarbonylfortimicin B-1,5-carbamate(3) $[\alpha]_D^{23} + 1011$ (c 1%, CH$_3$OH), NMR (CDCl$_3$) $\delta$1.14 d(J=3 HZ) (C$_{6'}$—CH$_3$), 2.36 (NHCH$_3$), 3.45 (OCH$_3$), IR (CDCl$_3$) 3529, 3439, 3324, 1712 cm$^{-1}$.

Analysis Calcd. for C$_{32}$H$_{42}$N$_4$O$_{10}$: C, 59.80; H, 6.59; N, 8.72 Found: C, 59.43; H, 6.72; N, 8.63

EXAMPLE 4

4-N-Acetyl-2',6'-di-N-benzyloxycarbonylfortimicin B-1,5-carbamate (4)

To a magnetically stirred solution of 7.5 g of 2',6'-di-N-benzyloxycarbonylfortimicin B-1,5-carbamate in 150 ml of tetrahydrofuran is added 2.5 ml of acetic anhydride. Stirring is continued at ambient temperature overnight. The resulting solution is shaken with a mixture of 200 ml of chloroform and 200 ml of 5 percent aqueous sodium bicarbonate. The chloroform solutions are combined and the chloroform is evaporated to leave the crude product which is chromatographed on a column of silica gel packed and eluted with ethyl acetate to provide pure product.

2-Deoxyfortimicin B can be prepared from a 1,5-carbamate of this invention using a general procedure developed by D. H. L. Barton et al., *J. Chem. Soc.*, Perkin I, 1574 (1975) and as outlined on Reaction Scheme II(4), (5), (6) and (7). Generally speaking, treatment of a carbamate of this invention with thiocarbonyldiimidazole in an inert solvent such as tetrahydrofuran, preferably in the presence of a tertiary amine such as triethylamine, gives the 2-O-thiocarbonylimidazole ester. Reduction with tri-n-butylstannane gives 2-deoxyfortimicin B-1,5-carbamate. Alkaline hydrolysis of the latter with, for example, potassium hydroxide in aqueous ethanol gives 2-deoxyfortimicin B.

The unprotected carbamates (R$_1$=hydrogen) are useful as analytical samples to confirm the identity of the intermediates of this invention.

We claim:

1. A 4-N-acylfortimicin B-1,5-carbamate represented by the formula

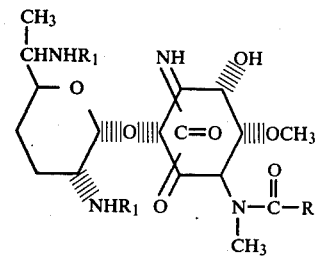

wherein R is acyl and R$_1$ is hydrogen or benzyloxycarbonyl.

2. A compound of claim 1 wherein R$_1$ is benzyloxycarbonyl.

3. A compound of claim 2 wherein R$_1$ is benzyloxycarbonyl and R is acetyl: 4-N-acetylfortimicin-2',6'-di-N-benzyloxycarbonylfortimicin B-1,5-carbamate.

4. A compound of claim 2 wherein R$_1$ is benzyloxycarbonyl and R is propionyl: 4-N-proprionyl-2',6'-di-N-benzyloxycarbonylfortimicin B-1,5-carbamate.

5. A compound of claim 2 wherein R is butyryl: 4-N-butyryl-2',6'-di-N-benzyloxycarbonylfortimicin B-1,5-carbamate.

6. A compound of claim 2 wherein R is valeryl: 4-N-valeryl-2',6'-di-N-benzyloxycarbonylfortimicin B-1,5-carbamate.

7. A compound of claim 1 wherein R is hydrogen.

* * * * *